(12) United States Patent  (10) Patent No.: US 7,771,408 B2
Mueller et al.  (45) Date of Patent: Aug. 10, 2010

(54) DIAPER WITH ELASTICATED TOPSHEET

(75) Inventors: Joerg Mueller, Karben (DE); Cornelia Martynus, Nidderau (DE); Anja Hoffmann, Hofheim (DE); Mattias Schmidt, Idstein (DE); John Costello, Wellesley, MA (US); Ann Sullivan, Waltham, MA (US); Gregg Flender, Bedford, MA (US)

(73) Assignee: The Procter & Gamble Company, Cincinnati, OH (US)

( * ) Notice: Subject to any disclaimer, the term of this patent is extended or adjusted under 35 U.S.C. 154(b) by 123 days.

(21) Appl. No.: 11/894,087

(22) Filed: Aug. 20, 2007

(65) Prior Publication Data

US 2008/0033388 A1  Feb. 7, 2008

Related U.S. Application Data

(63) Continuation of application No. 11/221,426, filed on Sep. 8, 2005, now Pat. No. 7,273,476.

(60) Provisional application No. 60/609,394, filed on Sep. 13, 2004.

(51) Int. Cl.
 *A61F 13/15* (2006.01)
 *A61F 13/20* (2006.01)
(52) U.S. Cl. ............... 604/385.24; 604/385.01; 604/385.09; 604/385.22; 604/385.23; 604/385.25
(58) Field of Classification Search ............ 604/385.24, 604/385.09, 385.01, 385.23, 385.25, 385.22
See application file for complete search history.

(56) References Cited

U.S. PATENT DOCUMENTS

| | | |
|---|---|---|
| 3,860,003 A | 1/1975 | Buell |
| 4,573,986 A | 3/1986 | Minetola et al. |
| 4,695,278 A | 9/1987 | Lawson |
| 4,795,454 A | 1/1989 | Dragoo |
| 4,808,178 A | 2/1989 | Aziz et al. |
| 4,892,536 A | 1/1990 | DesMarais et al. |
| 5,037,416 A | 8/1991 | Allen et al. |
| 5,176,672 A | 1/1993 | Bruemmer et al. |
| 5,269,775 A | 12/1993 | Freeland et al. |
| 5,342,342 A * | 8/1994 | Kitaoka ............ 604/385.19 |
| 5,531,730 A | 7/1996 | Dreier |
| 5,607,760 A | 3/1997 | Roe |
| 5,609,587 A | 3/1997 | Roe |
| 5,635,191 A | 6/1997 | Roe |

(Continued)

FOREIGN PATENT DOCUMENTS

EP  0908162 A  *  4/1999

(Continued)

*Primary Examiner*—Tatyana Zalukaeva
*Assistant Examiner*—Ginger T Chapman
(74) *Attorney, Agent, or Firm*—Richard L. Alexander; Amy M. Foust (57) ABSTRACT

The present invention relates to a disposable absorbent article, e.g. a diaper, having a backsheet, an absorbent core and a topsheet, said absorbent article having a length L, said topsheet having an opening and primary elasticated areas and secondary elasticated areas, the latter being curved or angled, having an overall curvature with a radius of from 0.3 L to 3.2 L, wherein the average transverse distance between a primary elasticated area and a secondary elasticated area of a crotch side portion is preferably at least 15 mm.

10 Claims, 8 Drawing Sheets

U.S. PATENT DOCUMENTS

| | | |
|---|---|---|
| 5,643,588 A | 7/1997 | Roe et al. |
| 5,779,690 A | 7/1998 | Gustafsson et al. |
| 5,817,086 A | 10/1998 | Kling |
| 5,947,947 A | 9/1999 | Tanzer et al. |
| 5,957,907 A | 9/1999 | Sauer |
| 6,102,892 A | 8/2000 | Putzer et al. |
| 6,132,409 A | 10/2000 | Vogt et al. |
| 6,454,750 B1 | 9/2002 | Vogt et al. |
| 6,482,191 B1 | 11/2002 | Roe et al. |
| 6,605,070 B2 | 8/2003 | Ludwig et al. |
| 6,616,648 B2 | 9/2003 | Hermansson et al. |
| 7,223,261 B2 | 5/2007 | Mueller et al. |
| 7,273,476 B2 | 9/2007 | Mueller et al. |
| 2004/0092900 A1 | 5/2004 | Hoffman et al. |
| 2004/0162538 A1 | 8/2004 | Mueller et al. |
| 2004/0193134 A1 | 9/2004 | Mueller et al. |
| 2006/0014460 A1 | 1/2006 | Alexander et al. |
| 2006/0189956 A1 | 8/2006 | Catalan |
| 2007/0093771 A1 | 4/2007 | Arizti et al. |

FOREIGN PATENT DOCUMENTS

| | | |
|---|---|---|
| EP | 1201212 | 5/2002 |
| EP | 1279388 | 1/2003 |
| EP | 1417945 | 5/2004 |
| EP | 1520569 | 4/2005 |
| FR | 2711057 A * | 4/1995 |
| JP | 04-150853 | 5/1992 |
| JP | 6-17726 | 3/1994 |
| WO | WO 9524173 | 9/1995 |
| WO | WO 03/009793 A1 * | 2/2003 |
| WO | WO 03/009795 A1 | 2/2003 |
| WO | WO 2005/004769 | 1/2005 |

* cited by examiner

DIAPER WITH ELASTICATED TOPSHEET

CROSS REFERENCE TO RELATED APPLICATIONS

This application is a continuation of U.S. application Ser. No. 11/221,426, filed Sep. 8, 2005 now U.S. Pat. No. 7,273,476, which claims the benefit of U.S. Provisional Application No. 60/609,394, filed Sep. 13, 2004, the substances of which are incorporated herein by reference.

FIELD OF THE INVENTION

This invention is directed to a disposable absorbent article, e.g. a diaper, having a backsheet, an absorbent core and a topsheet, said absorbent article having a length L, said topsheet having an opening and primary elasticated area, and secondary elasticated areas in the form of a curved or angled band, whereby each secondary elasticated area has an overall curvature with a radius of from 0.3 L to 3.2 L.

BACKGROUND OF THE INVENTION

A well-known problem with diapers is that feces, and in particular runny feces, may leak out of the diaper in use. A range of solutions has been suggested to better store feces in the diaper, including diapers with a topsheet with one or more openings, through which the feces can pass to a void space between the topsheet and the absorbent core. The problem with such diapers is that the opening is difficult to position correctly in use, such that the feces will actually pass through the opening and such that the opening does not close in use, in particular when the user (baby) moves around.

Hereto, diapers with topsheets with elastic bands along the opening or openings have been developed, whereby the elastic bands help positioning the opening(s) and keeping the opening in the correct place during use. For example U.S. Pat. No. 6,482,191 and US 2004/0162538A1 describe such diapers with an elasticated topsheet with an opening, which have an improved fit in use. Subsequent developments have provided diapers which an elasticated topsheet which is fully decoupled from the remaining part of the diaper, such that the topsheet would stay in contact with the skin even when the diaper is full and heavy and has a tendency to sag, as described in US 2004/0193134A1.

However, the inventors have now found that the fit of such diapers with openings including sag-tolerable diapers, known in the art, can be even further improved by providing the topsheet hereof with specific additional, secondary elastics, which are such that also an improved cross-machine direction elastic force is obtained, which ensures that the opening remains open in use and does not slip into the anus and which on the other hand also ensures that the opening remains aligned with the anus and close enough to the anus, herein referred to as "anchoring" of the topsheet to the skin of the user. The secondary elastics provide also an additional gasketing function, which further reduces the risk of any potential leakage of BM from the diaper.

SUMMARY OF THE INVENTION

The invention provides a disposable absorbent article having a backsheet, an absorbent core and a topsheet, said absorbent article having a length L, said topsheet having:

a) a pair of opposition longitudinal side edges; and
b) a front portion and a back portion; and
c) an opening, present in part of the front region and part of the back region, said opening having opposing longitudinal side edges and, adjacent each longitudinal side edge, a crotch side portion, said opening providing a passageway to a void space for receiving bodily exudates therein and said void space being positioned between the topsheet and the absorbent core, and each crotch side portion comprising a longitudinally extending primary elasticated area, wherein each crotch side portion of the topsheet comprises a secondary elasticated area, which is curved or angled, having an overall curvature with a radius of from 0.3 L to 3.2 L.

The absorbent article is preferably a sag-tolerable diaper or training pants.

DETAILED DESCRIPTION OF THE INVENTION

As used herein, the following terms have the following meanings:

As used herein, 'absorbent article' means any article that can absorb body fluids and is suitable to be placed in close proximity to the genitals of the user, including in particular and adult or infant diaper and so-called training or pull-up pants.

As used herein 'front region' and 'back region' refer to the two regions, which are in use, respectively, closest to the front of the wearer and the back of the wearer.

As used herein 'crotch side portion' is the portion of the topsheet between the longitudinal side edge of the opening and the longitudinal side edge of the topsheet, and the crotch side portion may thus be part of the front region and/or the back region.

As used herein, the term 'void space' is a cavity in the article present in at least the relaxed state, which serves to accept and contain bodily exudates such as fecal material, typically being at least 5 $cm^3$ in relaxed state.

When used herein, 'longitudinal' is the direction running substantially parallel to the maximum linear dimension of the component, typically to the longitudinal axis of the article, and includes directions within 30° of this parallel, when applicable.

The 'lateral' or 'transverse' direction is orthogonal to the longitudinal direction and in the same plan of the majority of the article and the longitudinal axis and includes directions within 30° of the orthogonal, when applicable.

'Extendibility' and 'extendable', when used herein, means that the width or length of the component (in relaxed position) can be increased.

As used herein, the term 'attached' encompasses configurations whereby a first element is directly secured to another element by affixing the element directly to a second element.

As used herein, the term 'joined' or 'connected' encompasses configurations whereby a first element is indirectly secured to a second element by affixing the first element to a third, intermediate member(s), which in turn are affixed to the second element.

As used herein 'stretched' or 'stretched state' means that the article or topsheet thereof is stretched to its maximum length, which is typically determined by the length of a non-elastically extendable component which is part thereof, e.g. the backsheet or the non-elastically extendable material of the topsheet.

As used herein 'relaxed' or 'relaxed state' means the state that no forces are applied to the article or component thereof (other than naturally occurring forces such as gravity), when the article is laid on a horizontal surface, such that the transverse front and back edge are flat on the horizontal surface and the transverse centre line or axis is on the horizontal surface.

As used herein, 'elasticated' means typically, that the component consists of or comprises elastic material, which is elastic in at least one direction. 'Non-elasticated' when used herein means that the component does not comprise any elastic material.

As used herein, 'along' means 'at least partially substantially parallel to and adjacent to'. Adjacent includes 'in close proximity with' and 'in contact with'.

As used herein, 'opening in the topsheet' means an area completely circumscribed by the topsheet, but where the topsheet material is not present, and which is large enough to receive fecal material, typically being at least 2 cm long or wide, or having a surface area of at least 2 cm$^2$.

As used herein, 'sag-tolerable' means that the topsheet does substantially not sag and maintains its z-direction and preferably x- and y direction alignment, as described herein after.

The absorbent article of the invention comprises one or more openings, but preferably a single opening for the reception of fecal material. Preferably, the opening is in the form of a longitudinally extending opening, a so-called slit opening. The opening is preferably present in the centre region of the topsheet, and extends optionally into the front region (in use towards the front of the user) and/or into the back region of the topsheet.

Preferably, the topsheet has a slit opening, which has a longitudinal dimension (length) substantially parallel to the longitudinal axis of the topsheet and of the diaper.

Preferred is that (in stretched state) the opening (or openings) of the topsheet is (are) configured such that from 20% to 40%, or more preferably from 20% to 30% of the length of the opening (or total length of the openings) extends from the transverse axis of the topsheet towards the front edge of the topsheet (i.e. present in the front region) and the remaining percentage extends towards the back edge of the topsheet (i.e. present in the back region).

The dimensions and exact shape of the opening(s) may vary, depending on the size of the topsheet and/or the absorbent article. For example, in a preferred embodiment the opening is in the form of a slit opening with substantially parallel longitudinal side edges. In a preferred embodiment, the longitudinal side edges of the slit opening are connected in the front and in the back by V-shaped edges, or rounded V-shaped edges (each of the V-shaped edges being two angled edges). Preferably, the front V-shaped edges have a larger angle than the back V-shape edges. Preferably, the front V-shaped edges have an angle of 20° to 140°, preferably from 45° to 65°, most preferably from 55° to 60°, as described herein after and can be seen from FIGS. 1, 2, 4 and 5.

Figure 3:
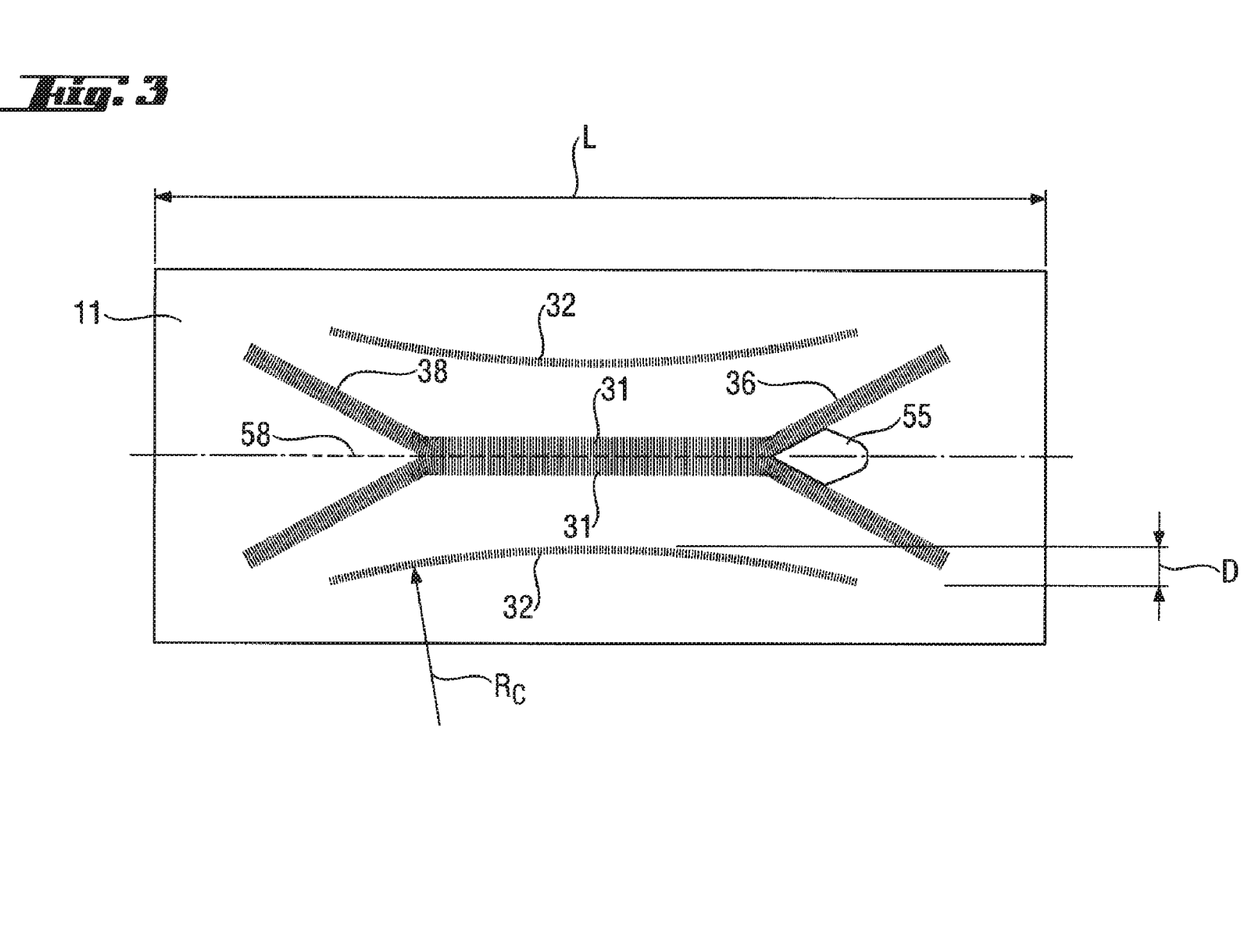
FIGS. 3 and 6 show each how the slit opening may be cut in the topsheet and how the radius of the secondary elasticated areas is determined.
Figure 6:
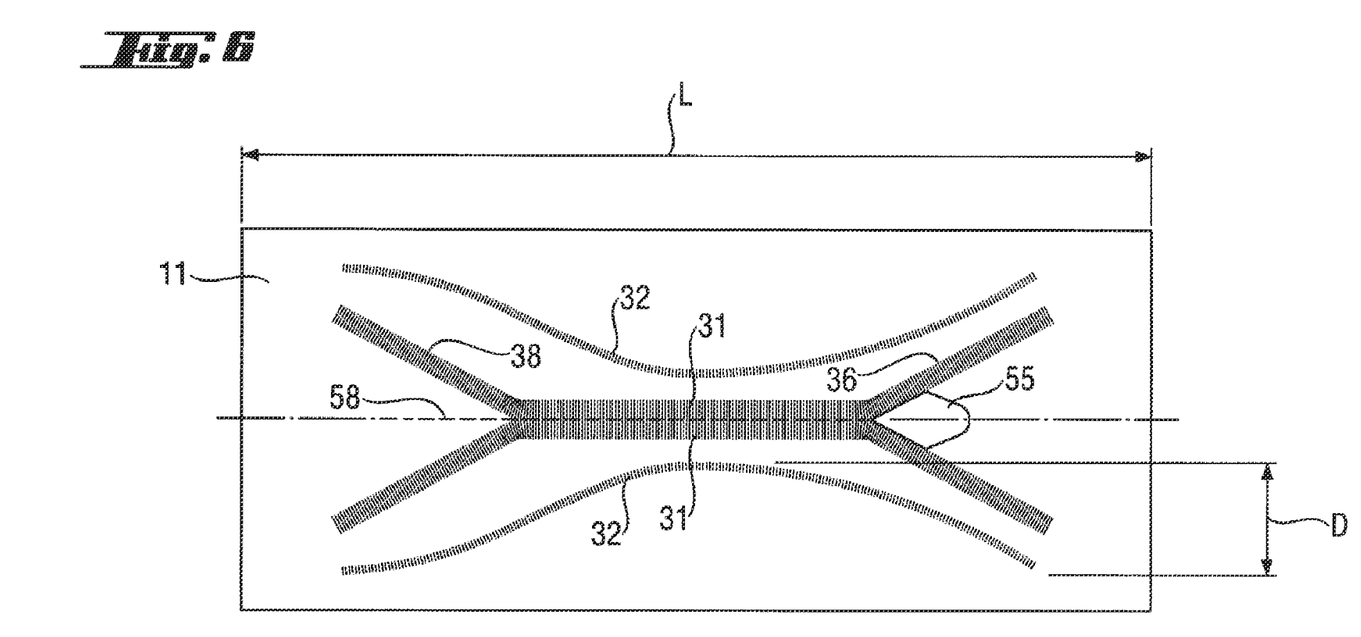

As also shown in FIGS. 3 and 6, the slit made to form the slit opening, may optionally extend into an additional cut-out area which is for example diamond shaped, as described herein after, to obtain the above-mentioned V-shaped edges in the front region of the absorbent article.

The maximum length of the slit opening may be for example 40% to 90% or more preferably 50% to 80%, or even more preferably about 60% to 70%, of the total length L of the absorbent article.

In certain size 4 diapers with a maximum topsheet length of between 45 cm and 55 cm (typically between 48 cm and 52 cm) the length of the single slit opening, when the diaper is in stretched state, is from 20 cm to 40 cm, or even from 25 cm to 35 cm, or even from 28 cm to 32 cm.

The average width of the opening of the absorbent articles herein, in stretched state, is preferably from 5% to 30%, or more preferably 10% to 25%, or more preferably about 15% of the average width (including opening) of the topsheet, or for example for a size 4 diaper, 15 mm to 60 mm, more preferably from 20 mm to 40 mm.

The topsheet comprises adjacent each longitudinal side edge of the opening or openings a crotch side portion (i.e. each longitudinally extending, between a longitudinal side edge of the opening and a longitudinal side edge of the topsheet), each comprising a primary elasticated area and a secondary elasticated area, preferably being spaced apart with an transverse average distance of at least 15 mm, preferably at least 20 mm or even more preferably at least 25 mm. The minimum transverse distance between a primary and secondary elasticated area of the same crotch side portion is preferably 0.5 mm, or preferably at least 5 mm.

The primary elasticated area is preferably directly adjacent the longitudinal side edge of the opening, or part thereof.

Preferred primary elasticated areas are described in US 2004/0162538A1.

An elasticated area in the topsheet may be formed from a multitude of thin strands of elastic material or for example from a single band of elastic material.

The primary elasticated areas are preferably longer than the opening. The primary elasticated areas extend preferably from the crotch side portion of the topsheet, towards or completely to the front and back edge of the topsheet, typically over at least 70% of the length of the topsheet. For example, for a size 4 diaper, the primary elasticated area may be at least 35 cm, preferably from 35 to 45 cm.

The width of the primary elasticated areas on the topsheet will vary, typically depending on the exact dimensions of the topsheet and/or the article.

For example, for size 4 diapers as described above, a primary elasticated area, in stretched state, may be an elastic band, or a multitude of elastic strands, such that each elasticated area has an average width of about 3 mm to 50 mm, preferably 3 mm to 40 mm, or even more preferably 3 mm to 20 mm, or more preferably 5 mm to 20 mm.

Each primary elasticated area is shaped such that it has a centre portion with a length L2, which may be at least partially substantially parallel to the centre portion of the opposing primary elasticated area, also with a length L2, whereby L2 is 30% to 70% of the total length L1 of the elasticated area; hereby, it is preferred that the total length of the elasticated area L1 is about 70% to 90%, or preferably from about 80% to 90% or preferably about 85% of maximum length of the topsheet.

Preferred is that the front end portions of two opposing primary elasticated areas bend away from one another (in the plane of the topsheet), so that the distance between the end edges of the opposing front end portions of two opposing elastic areas is larger that the distance between the centre portions of two opposing elastic areas. Equally, it is preferred that the back end portions of opposing primary elasticated areas bend away from one another and that the distance between the end edges of the opposing back end portions of two opposing elastic areas is larger that the distance between the centre portions of two opposing elastic area.

Then, each front end portion of a primary elasticated area has typically an angle with a line parallel to the longitudinal axis of the article and through the centre portion elasticated area, of between 10° and 40°, or preferably 17° to 35°, or preferably 20° and 35°, and each back end portion of a primary elasticated area has also typically an angle with the line parallel to the longitudinal axis of the article and through the centre portion of the elasticated area, between 10° and 40°, or preferably 17° to 35°, or preferably 20° and 35°. When both front end portions and both back end portions have an angle as above, then the primary elasticated areas have, as is herein referred to, an X-shape, and a preferred X-shape is exemplified in FIGS. 1, 2, 4 and 5, as described herein after.

It may be that the front end and/or the back end and/or the centre portion of an elasticated area are curved rather than straight, and then the angles above are determined by the angle of the tangent line through the centre point of the front end and/or back end, with the line parallel to the longitudinal axis of the topsheet and tangent to the centre point of the centre portion of the elasticated area.

The inventors also found that the 'anchoring' of the topsheet to the wearer's body may be improved by this specific manner in which the primary elastics are positioned The primary elasticated areas and secondary elasticated areas may be in the topsheet material or attached to the top surface or bottom surface of the topsheet. Preferably, they are such that they are not in direct contact with the skin of the user.

Each of the pair of secondary elasticated areas is being comprised by at least the crotch side portions of the topsheet, but preferably each secondary elasticated area preferably extends towards the transverse front edge and back edge of the topsheet, but typically not completely to these edges.

The secondary elasticated areas have a curvature with a specific radius. For the purpose of the invention the overall curvature is the curved line through the two end points of a secondary elasticated area and through the point on the same secondary elasticated area that is transversely closest to the primary elasticated area of the same crotch side portion (herein referred to as 'closest point'), whereby the two end points are always further apart from the primary elasticated area than said closest point, or in other words, an end point is never the closest point. An end point of a secondary elasticated area is herein the point of the transverse end edge of the secondary elasticated area, which is transversely closest to the longitudinal side edge of the topsheet. This curved line has a radius R with a length of between 0.3 times the length of the absorbent article (L) to 3.2 times the length of the article, i.e. the radius is 0.3 L to 3.2 L, or preferably 0.4 L to 2.8 L.

For completeness, the overall curvature of a secondary elasticated area is away from the primary elasticated area, which typically means that the overall curvature is such that the closest point is present in the centre region of the elasticated area.

Thus, the secondary elasticated area may be a perfect curved line, or it may be two straight lines connected to one another under an angle (herein referred to as 'angled'), or a curved line with an inflection point (as shown in for example FIG. 2), etc.

The transverse distance of this closest point to the primary elasticated area is preferably at least 0.5 mm, preferably between 0.5 mm and 30 mm, or even more preferably between 3.0 mm and 20 mm.

The end points of each secondary elasticated area are preferably close to the longitudinal side edges of the topsheet, but preferably not in contact with the longitudinal side edges of the topsheet, preferably the transverse distance between the longitudinal side edges and an end point being at least 5.0 mm, preferably at least 10 mm. Preferably, the end points of a secondary elasticated area are close to the transverse edge of the topsheet, but preferably not in contact with the transverse end edge of the topsheet, the longitudinal distance between an end point and the transverse end edge of the topsheet being preferably between 1 and 20% of the total length of the topsheet and/or of the article, more preferably between 5 and 15% or even between 9% and 13% of the total length of the topsheet and/or the article (length L).

Preferably, the average transverse distance between the primary and secondary elasticated area of a crotch side portion is at least 15 mm, or more preferably at least 20 mm or even more preferably at least 25 mm, this average being the average of 3 distances, namely the transverse distance from the closest point (of the secondary elasticated area) to the primary elasticated, the transverse distance from the front end point (of the secondary elasticated area) to the primary elasticated area, and the transverse distance from the back end point (of the secondary elasticated area) to the primary elasticated area, i.e. the 3 transverse distances of the 3 points that determine the curvature of the secondary elasticated area.

Preferably, the secondary elasticated area does not comprise any angles and it is curved over its full length, with a single curvature, optionally with an inflection point.

The average width of a secondary elasticated area, e.g. a multitude of strands or a single band of elastic material, is preferably from 0.5 to 20 mm or even from 0.5 to 10 mm.

The length of a secondary elasticated area will depend on the length of the article and the topsheet thereof, and the elastic cross machine direction (CD) force required, e.g. the curvature required and distance to the primary elasticated area required, as mentioned above.

The topsheet comprises preferably also one or more tertiary elasticated areas. A tertiary elasticated area is then present between a secondary elasticated area and a longitudinal side edge of the topsheet, and preferably spaced apart from the closest secondary elasticated area with an average transverse distance of at least 5 mm, or preferably at least 10 mm, or even more preferably at least 15 mm.

The tertiary elasticated areas are preferably also curved with an overall curvature as described above for the secondary elasticated area, but whereby the minimum radius is 0.1 L.

The elasticated areas herein are typically in the form of a multitude of strands or a single band of an elastic material with an average thickness (e.g. gauge) of at least 20 microns, more preferably at least 40 microns, or even at least 60 microns, typically up to about 300 microns, or even up to 200 microns or even up to 150 microns. Highly preferred materials have an average thickness of about 70 to 100 microns.

Preferred elastic materials used hereto include VFE-CD, available from Tredegar, and L-86, L-89, or L-90, available from Fulflex (Limerick, Ireland).

Preferably, the elasticated areas herein are formed by attaching an elasticated material in stretched state or partially being in stretched state to the topsheet, or to one or more carrier material(s), which is (are) then subsequently attached to the topsheet.

The absorbent article of the invention is preferably sag-tolerable, and it thereto has preferably a topsheet that is sag-tolerable, as defined in co-pending application US 2004/0193134A1.

This means that the topsheet does not sag and that the topsheet keeps its z-direction alignment with the anal region and genitals of the wearer, and typically also its x and y direction alignment, when the backsheet and absorbent core sag due to increased weight of the body exudates received by the article. The absorbent article, preferably diaper or training pants, has thereto means to ensure that the topsheet stays in about the same contact or close proximity with the wearer's anal and/or genital region when the backsheet and core sag, compared to just after application of the article to the wearer, when the backsheet and core do not yet sag. Typically the topsheet is sag-tolerable to such an extend that when the geometrical centre point of the backsheet is pulled down with 4 cm, the topsheet does not move down with more than 0.5 cm, or even not more than 0.25 cm, or typically the topsheet does not move down at all, and/or such that the longitudinal side edges of the opening do not move in the x and y direction with more than 0.5 cm, or preferably not more than 0.25 cm, or does not move at all.

The longitudinal side edges of the topsheet are preferably joined or attached to the longitudinal side edges of the backsheet, by any attachment means known in the art, to form longitudinal opposing attachment areas. In one preferred embodiment of the present invention, the topsheet and the backsheet are attached directly to each other in some locations and are indirectly joined together in other locations.

Preferably, the average width of the topsheet, including the width of the opening, is larger than the average distance between the longitudinal attachment areas of the topsheet to the backsheet, mentioned above. Also preferred may be that the average width of the topsheet, including the width of the opening, is larger than the average width of the backsheet. The topsheet may for example have one or more transverse and/or, more preferably, longitudinal folds, which can unfold in use and allow sagging of the core and backsheet, while the topsheet remains in place.

The topsheet herein may be liquid or urine pervious or impervious. It may be preferred that the topsheet is liquid or urine pervious in one direction, but liquid or urine impervious in the opposite direction, e.g. that body fluids may penetrate through the topsheet to the remaining part of the diaper, but that no or limited amounts of liquid (urine) can penetrate in reverse direction, towards the wearer's skin.

However, in a highly preferred embodiment, the topsheet or at least more than 50% of its surface area (that faces the wearer in use) is hydrophobic. Preferred is that the topsheet is urine impermeable and faeces impermeable. Thereto, the topsheet is for example made of a material having a Strike Through time for the first gush of more than 120 seconds, as determined by the test method described hereinafter. Preferred topsheets herein are considered urine-impermeable and feces impermeable and thus suitable herein, when they have a low surface energy and a uniform pore size distribution, preferably with the surface energy values, pore sizes and air permeability values described in co-pending application EP-A-1417945. Preferred are materials with an alcohol repellency of at least 7 or more preferably at least 8 or even more preferably at least 9, or even more preferably at least 10; preferably having a surface energy of less than 25 mN/m; preferably having a contact angle with water of above 130°; and preferably having a mean pore size of less than 20 microns, preferably less than 17 microns, or most preferably less than 13 microns, but preferably at least 2 microns, or preferably at least 5 microns. Preferably, the topsheet has an air permeability of at least 3 Darcy, or preferably at least 10 Darcy, or even more preferably at least 20 Darcy, or even more preferably at least 30 Darcy, or even most preferably 50 Darcy.

Thereto, preferred topsheets herein are made of hydrophobic material or are treated to be hydrophobic (in order to isolate the wearer's skin from liquids contained in remaining part of the diaper), with for example a hydrophobic surface coating. Preferred hydrophobic surface coatings are for example described in co-pending application U.S. Ser. No. 11/055743, filed Feb. 10, 2005. Preferably, the hydrophobic surface coating comprises one or more silicone polymers or fluorinated polymers. Suitable silicone polymers are for example selected from the group consisting of silicone MQ resins, polydimethysiloxanes, crosslinked silicones, silicone liquid elastomers, and combinations thereof. Typically, the molecular weight of such silicone polymers should be at least about 4000 MW, preferably at least about 10,000 MW, more preferably at least about 15,000 MW, even more preferably at least about 20,000 MW, and most preferably at least about 25,000MW. Preferred polydimethylsiloxanes are selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof. Suitable fluorinated polymers are selected from the group consisting of telomers and polymers containing tetrafluoroethylene and/or perfluorinated alkyl chains. For instance, fluorinated surfactants, which are commercially available from Dupont under the tradename Zonyl®, are suitable for use herein. In particular, Zonyl® 321, 329, 8740, 9027, and 9360 are well suited for use in the present invention. Additionally, other Zonyl® materials include fluroadditives like micro-powders may be useful herein. These include, but are not limited to Zonyl® MP1100, MP1200, MP1400, MP1500J, MP1600N, TE-3667N (which is a water dispersion). Preferably, the coating is free of aminosilicones.

These materials are preferably deposited onto the topsheet in amounts of from at least about 0.01 gsm (gram of material/square meter of topsheet), more preferably from at least about 0.05 gsm, and most preferably from at least about 0.1 gsm.

A suitable topsheet may be manufactured from a wide range of materials, including woven or non-woven webs of natural fibers (e.g., wood or cotton fibers) or synthetic fibers (e.g., polyester, polyethylene and/or polypropylene fibers), or a combination of natural and synthetic fibers. If the topsheet includes fibers, the fibers may be for example spun bond, carded, wet-laid, melt blown, hydro entangled, or otherwise processed as is known in the art.

Preferred are materials that are compliant, soft feeling, and non-irritating to the wearer's skin.

Highly preferred are webs comprising spunbond layers (S) and meltblown layer(s) (M), whereby the surfaces of the web are formed by spunbond layer(s). Preferred are such webs with a relatively high basis weight, for example more than 25 gram/$m^2$ (gsm), for example 34 gsm SMMS (whereby 12 gsm meltblown and 5 gsm spunbond); 34 gsm SMMS (whereby 10 gsm meltblown and 7 gsm spunbond); 30 gsm SMMS (whereby 10 gsm meltblown and 5 gsm spunbond); 30 gsm SMMS (whereby 8 gsm meltblown and 7 gsm spunbond); 34 gsm SMS (whereby 20 gsm meltblown and 7 gsm spunbond), or for example webs comprising two layers of 17 gsm SMMS, described above.

Any portion of the topsheet may be coated with a lotion or powder as is known in the art. Preferred may be that at least lotion is present on the primary elasticated areas, and even preferably on the secondary elasticated areas. The lotion used on one elasticated area may be different to the lotion used on another elasticated area, or on the remaining part of the topsheet. Examples of lotions include those described in U.S. Pat. Nos. 5,607,760; 5,609,587; 5,635,191; 5,643,588; WO 95/24173, provided the lotion is compatible with the elastic material, and does not destroy the elastic material or reduce its elasticity.

The absorbent article may comprise a genital coversheet, which in use covers the genitals and protects the genitals from being soiled by faeces. The genital coversheet is preferably present under, in or above the opening in the topsheet, typically only that part of the opening that is in close proximity with the genitals during use, i.e. the front region of the opening. Preferably, the maximum length of the part of the genital coversheet that is present above, in or under the opening genital is 10% to 50% of the maximum length of the opening, preferred 10% to 30%, or more preferably 13% to 28% or even more preferably 17% to 27%. In other words, at the most 50% of the maximum length of the opening is 'covered' by the longest part of the genital coversheet, but at least 10% of the maximum length of the opening is covered by the longest part of the genital coversheet.

Preferably, the genital cover sheet has a substantially transverse edge above, in or under the opening which is not straight, but preferably curved or V-shaped (arrow shaped), having the centre point of the curved edge or of the V-shaped edge closer to the front of the article than the remaining part of the curved edge or V-shaped edge. Then, the length of the part of the genital coversheet from this centre point to the front of the opening is preferably 13% to 27% of the maximum length of the opening, more preferably 15% to 20%.

When the genital coversheet is preferably present under the topsheet and below the opening, thus between the topsheet and the absorbent core, then, the genital coversheet is typically not attached to the absorbent core, to ensure the creation of a maximum void space for fecal material between the topsheet and the absorbent core and between the genital coversheet and the absorbent core.

Preferably, the genital coversheet is partially attached to the topsheet, forming hereby attachment areas and non-attached area(s), the latter being typically above, in or under the opening. The non-attached area(s) may then form the protective genital cover for the genitals, typically in the form of a pocket.

The genital coversheet is extendable, either longitudinal or transverse or both, so that the pressure of the genitals onto the genital coversheet causes the genital coversheet to extend and form a pocket, positioned (partially) around the genitals. The genital coversheet may be elastically extendable, or preferably, the genital coversheet may be non-elastically extendable, in longitudinal and/or, more preferably, in transverse direction. Hereto, the genital coversheet is preferably attached, for example to the topsheet, with a pair of opposing attachment areas, with herein between one or more unattached area (s), as described above, whereby the average width of the unattached area (s) of the genital coversheet, between the pair of attachment area(s), is larger than the average distance (width) between the two attachment area, preferably at least 1.2 times larger, or even 1.5 times larger.

In yet another embodiment of the invention, the genital coversheet may be an integral part of the topsheet with the opening. Then, the genital coversheet is herein referred to as a genital cover portion of the topsheet. This integral genital coversheet or genital cover portion is then urine permeable and the remaining part of the topsheet (the faeces-retaining portion) is urine impermeable, as described herein after. The urine permeable genital cover portion is present in the front region of the topsheet, preferably between the front edge of the topsheet and the front edge of the opening, whilst part of the back region of the topsheet comprises said opening and the faeces-retaining portion.

Then, the genital cover portion is typically the front 10% to 50%, or more preferably 15% to 30%, or more preferably to 20%, of the surface area of the topsheet, while the fecal-material retaining portion, being the back portion of the topsheet, is the remaining percentage of the surface area of the topsheet.

It may also be preferred that the genital cover portion of the topsheet is extendable, preferably (at least) in transverse direction.

The genital coversheet is preferably urine permeable. Urine permeability can be determined by the Strike Through test, Edana test method 150.3-96, which is modified in that it applies 2 gushes of 5 ml at the same sample with a waiting time of 60 seconds between 2 gushes (without changing the absorbent pad) and in that the absorbent pad consists of 10 plies of filter paper, rather than 5 plies; the filter paper used may be Ahlstroem grade 989, or equivalent; the pick-up paper may be Ahlstroem Grade 632 or equivalent. This modified Edana test method provides the strike through times of the first gush and second gush, which are each an average of the values obtained in 3 tests.

Typically, the genital coversheet has an average urine permeability of the first gush strike through time of less than 7 seconds, preferably less than 5 seconds, or more preferably less than 3 seconds, and most preferably between 1 and 3 seconds or most preferably between 1 and 2 seconds. Preferably, the genital coversheet has a second gush strike through time of less than 9 seconds, preferably less than 7 seconds, or more preferably even less than 5 seconds, and preferably between 1 and 7 seconds or more preferably between 2 and 5 seconds.

Preferably, the genital coversheet does not allow moisture to pass back to the skin, and thereto, it preferably has a low rewet. This can be determined by the Wetback Test, Edana test method 151.3-02, under 23° C. and 50% humidity test conditions, as specified in the Edana test, and using a filter paper with a loading factor of 3.30, as specified therein, and resulting in average rewet values, which are an average of 3 test results (the filter paper used may be as specified above). Preferably it has an average rewet value of less than 0.8 g, preferably less than 0.5 g, more preferably less than 0.3 g, or even more preferably less than 0.2 g or even less than 0.15 g.

Also preferred may be that the genital coversheet can let low viscosity fecal material pass through and entangle it, thereby protecting the genitals from said fecal material. Preferred is thereto that the genital coversheet is formed from materials with large pores, and large caliper, e.g. an a mean pore size of 50 to 400 microns, or even more preferably from 100 to 300 microns, and an average caliper of 0.5 to 1.5 mm, preferably 0.7 mm to 1 mm, such as carded resin-bonded or air-through nonwovens made of for example PET fiber.

Preferred genital coversheets are thereto hydrophilic, or treated with a hydrophilising agent to render them hydrophilic. Preferred materials for the genital coversheet are nonwoven and woven materials comprising hydrophilic fibers and/or nonwoven or woven materials treated with a hydrophilising agent, e.g. a surfactant.

A preferred genital coversheet is also soft to touch. Thereto, it may be preferred that at least the surface in contact with the genitals is formed by a carded or spunbond material.

Preferred are for example spunbond nonwovens, laminates of spunbond nonwovens (S) and meltblown nonwovens (M), such as SM and SMMS laminates, or carded nonwovens, or apertured and/or formed films, such as for example described in U.S. Pat. Nos. 6,231,948; 6180,052, and 6,025,049, which each may be coated with a surfactant.

The absorbent article also comprises a, typically liquid impervious, backsheet, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to the topsheet, the absorbent core, or any other element of the diaper by any attachment means known in the art. It may be highly preferred that the longitudinal side edges of the topsheet and backsheet are directly attached to one another, but that the longitudinal edges of the topsheet and the core are not attached to one another.

The attachment means to attach the topsheet and the backsheet, but also the genital coversheet herein may include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core may comprise any absorbent material which is generally compressible, conformable, non-irritating to the wearer's skin, and capable of absorbing and retaining urine, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials; preferred may be absorbent cores which have an absorbent storage layer which comprises more than 80% by weight of the absorbent core content (e.g. excluding core wrap) of absorbent gelling material, and which is preferably free of airfelt, i.e. 100% absorbent gelling material.

The absorbent article may also include a sub-layer disposed between the topsheet and the absorbent core, capable of accepting, and/or immobilizing bodily exudates, typically fecal material. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, preferably looped, strands of fibers, or preferably apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

The absorbent article herein is preferably a disposable adult or infant diaper or training pants/pull-up pants. Diapers or training pants of the invention may have side panels, and/or more preferably one or more pairs of elasticated leg cuffs that provide improved containment of liquids and other body exudates. Leg cuffs may also be referred to as leg bands, side flaps, barrier cuffs, or elastic cuffs, as described in; U.S. Pat. Nos. 3,860,003; 4,808,178; 4,695,278 and 4,795,454.

The diapers herein preferably have a fastening system, typically joined to the waistband, as known in the art. Preferred fastening systems comprise fastening tabs and landing zones, wherein the fastening tabs are attached or joined to the back region of the diaper and the landing zones are part of the front region of the diaper.

Process to Make a Diaper of the Invention

A topsheet with an opening, typically along its longitudinal axis, and primary elasticated areas and a genital coversheet may be obtained as follows.

A longitudinally extending (slit) opening may be formed (cut) in the topsheet material first and a pair of primary elastic bands are attached, in stretched state, to the topsheet, so that an elastic band is present adjacent or in close proximity of each longitudinal edges of the opening. Alternatively, the primary elastic bands are first attached to the topsheet in stretched state, extending longitudinally over the topsheet, for example an X-shape, whereafter an longitudinally extending (slit) opening is formed (cut) through part of the topsheet material and part of the elastic bands, typically along the longitudinal axis of the topsheet material and the strands or bands.

Preferred adhesives for attaching the primary elastic strands or bands include H2031, available from ATO-Findley and HL-1620 available from H.B. Fuller (St Pauls, USA).

In a non-limiting example, two elastic band of L-89 elastic material, available from Fulflex, with (in relaxed state) a thickness of about 0.1 mm, a width of 20 mm and a length of 17 cm, are obtained and also a sheet of a polypropylene nonwoven material, for example available from Fiberflex, BBA and Pegas.

In stretched state, a slit opening with a length of between 25 cm and 35 cm, typically about 31 cm to 33 cm is cut in the nonwoven. This may be cut as a slit, whereby the slit opening obtains its width due to the spreading elasticated areas, or the slit opening may be cut with a width dimension, for example up to 4.0 cm. Typically, the slit opening is cut as a slit without width dimension, but in the front region of the topsheet, end the front point of the slit opening, an additional diamond shaped cut is made, as can be seen in FIGS. 3 and 6.

If the elastic areas are present on the surface of the topsheet which is in contact with the skin of the user, it may be preferred that an additional layer, e.g. nonwoven material, is placed on the elastic areas, to avoid direct contact by the elastic areas with the skin.

The centre portion of 9 cm of the primary elastic bands are stretched to 336% of the original length and then attached to the topsheet material. The two 4 cm end portions are attached in unstretched state. One elastic band is glued in a stretched state to each longitudinal edge of the opening of the non-woven.

Each elastic band is glued on the non-woven in a manner that the front end region of one elastic band bends away from the front end region of the opposing elastic band, and the back end region of one elastic band bends away from the back end region of the opposing elastic band, in the shape of an X. This is done such that, after application, the transverse distance between to the edges of the front end regions is for example 80 mm in stretched state, and the transverse distance between the centre points on the bands, in stretched state, 40 mm.

The angle of the front end region with the longitudinal line through the centre region of an elastic band, and parallel to the longitudinal axis of the topsheet, as described above and can be seen in FIGS. 2, 3, 5 and 6 as angle α, is for example, about 200. The angle of the back end region, as described above and can be seen in FIGS. 2, 3, 5 and 6 as angle β, is for example, about also 20°.

The longitudinal distance from an end edge of a primary elasticated area to the transverse front edge of the absorbent article or the transverse back edge of the absorbent article, which ever applicable, is typically about 50 mm.

Then, a secondary elastic band is attached to the topsheet, between each primary elastic band and the closest longitudinal edge of the topsheet, such that the secondary elastic band is curved as described herein.

Then, a genital coversheet may be attached to the topsheet in stretched state, such that the front 15% to 30% of the opening is covered by the genital coversheet. The genital coversheet has preferably a curved or V-shaped edge above the opening. The genital coversheet is for example attached to the surface of the topsheet which is not in contact with the skin of the user, with at least two longitudinal areas (lines, spirals, dots) of adhesive, each being between a longitudinal edge of the topsheet and a primary elastic band, e.g. about 0.5 to 1.5 cm spaced away from said elastic band. The distance between the two substantially parallel attachment areas is at the most about half the width of the genital coversheet between these areas, so that the genital coversheet hangs downwards in use, under the opening, as a pocket for the genitals.

The topsheet may be used on a Pampers Premium Size 4 diaper, designed for a baby weight range of 21-37 pounds, or it may replace the layer of a Pampers premium Size 4 diaper which is on the absorbent core and in use in contact with the skin of the baby. Thereto, the topsheet with the elastic bands are attached to the front and back waistbands, and typically to the longitudinal side edges of the backsheet.

DESCRIPTION OF THE FIGURES

Figure 1:
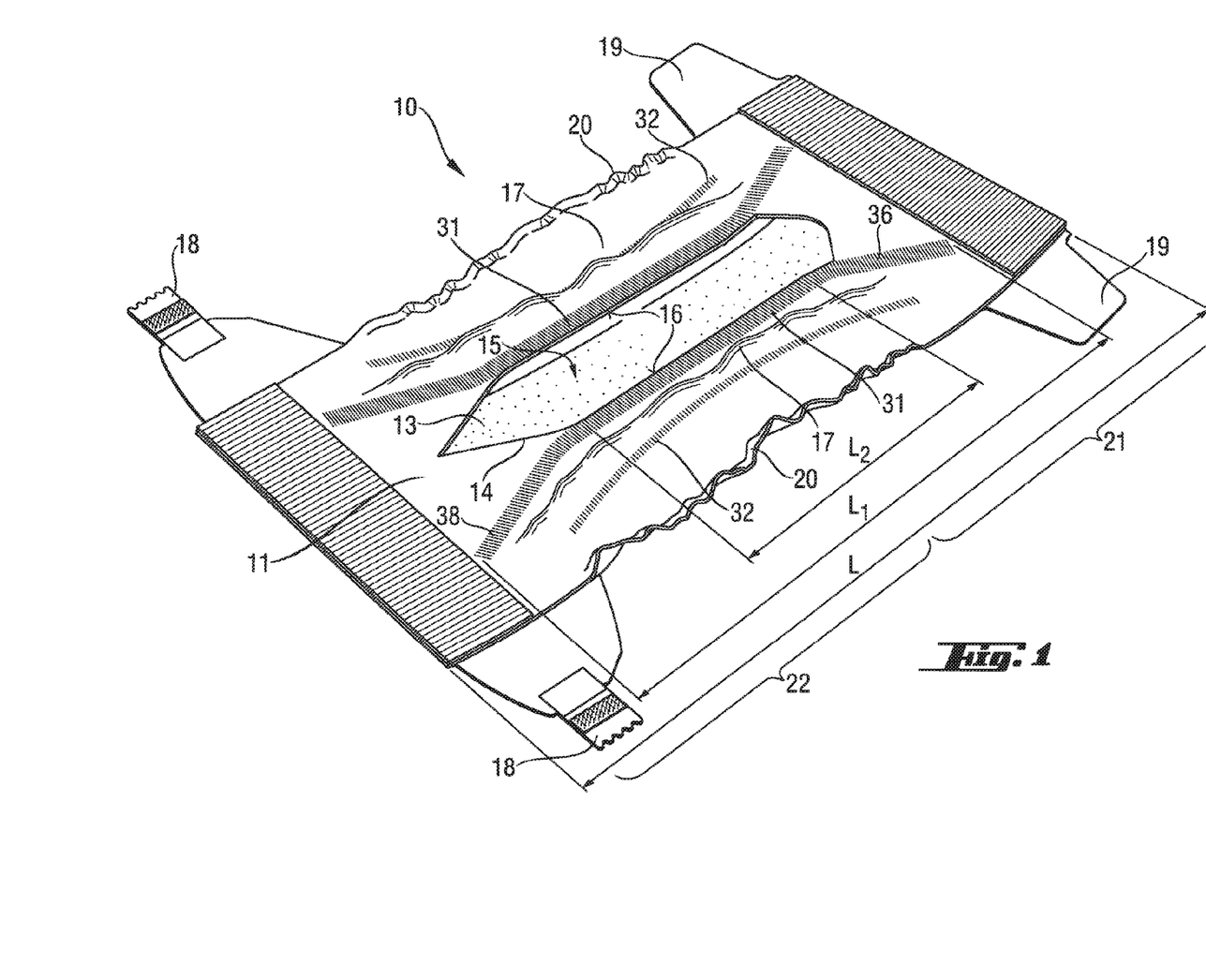
FIGS. 1 and 4 show each a perspective view of two preferred absorbent articles of the present invention.
Figure 4:
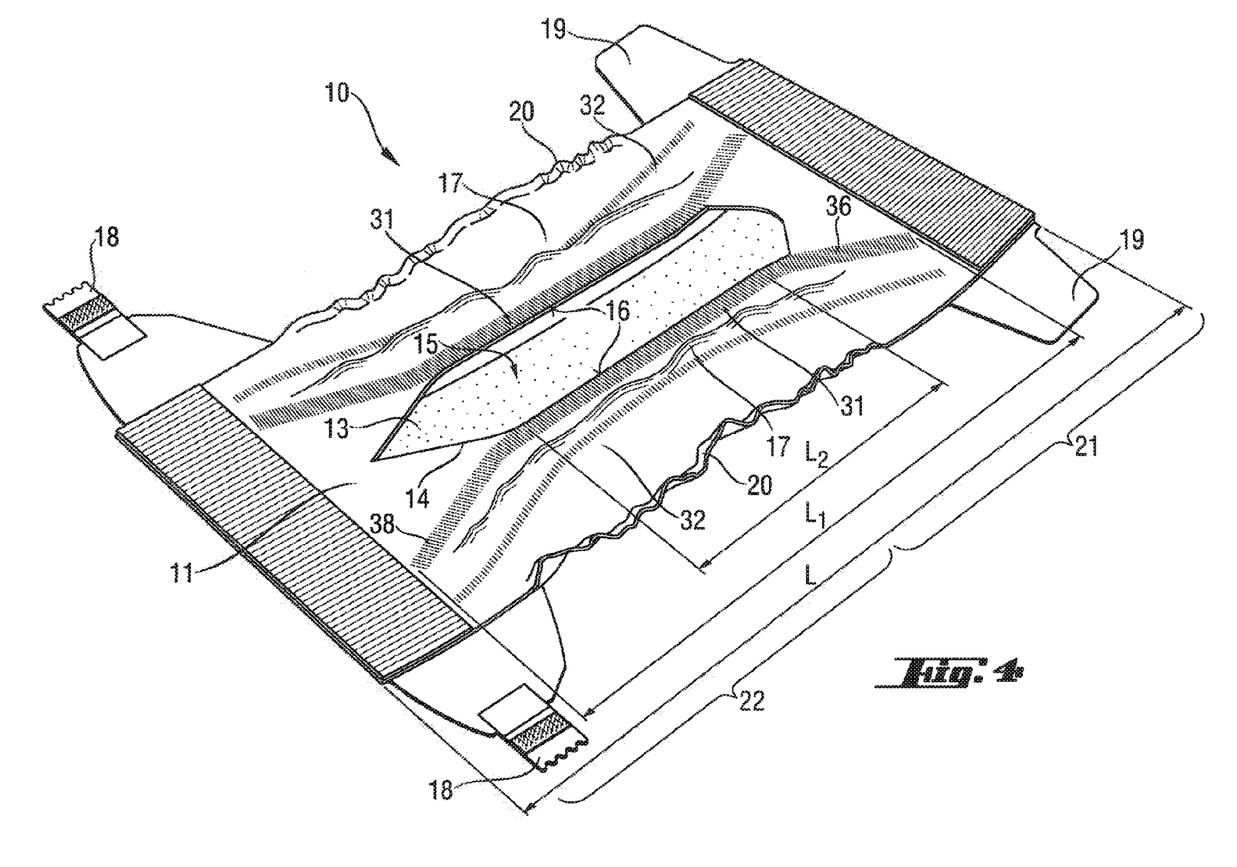

FIGS. 1 and 4 show each a perspective view of a preferred absorbent article (10), a diaper (10), of the present invention with a front region (21) and back region (22) and with an opening (14) in said topsheet. A void space (15) is present between the absorbent core (13) and the topsheet (11).

The diaper (10) typically comprises also a back waist band with a pair of ears with fasteners (18) and a front waist band (19) with receiving areas for the fasteners. Typically, the fasteners comprise hooks and/or adhesive and the receiving areas are preferably formed from loop-containing material.

As described above, the topsheet (11) is typically sag-tolerable and thereto non-elastically extendable and it preferably has thereto one or more transverse folds and/or more preferably longitudinal folds (17).

The topsheet (11) is elasticated, having primary elasticated areas (31) positioned along the longitudinal side edges (16) of the opening (14). The topsheet (11) also has secondary elasticated areas (32), and it may even have tertiary elasticated areas (33). The secondary elasticated areas (32) are substantially curved, having a curvature with a radius R, as defined herein and shown in FIG. 3.

The secondary elasticated area (32) shown in FIG. 4 has an inflection point towards the back region (22) of the topsheet (11).

The primary elasticated areas (31) have each a centre region, whereby this pair of centre regions are preferably substantially parallel to one another, and whereby each centre region has a length L2, which is typically about 30% to 70% of the total length L1 of the primary elasticated areas (31), and preferably about 40% to 80% of the maximum length of the slit opening. The primary elasticated areas (31) are preferably in an X-shape, whereby the front end portions (36) bend away from one another and the back end portions (38) bend away from one another.

The diaper (10) typically also comprises elasticated bands along the longitudinal side edges of the diaper (10), so called leg cuffs (20).

Figure 2:
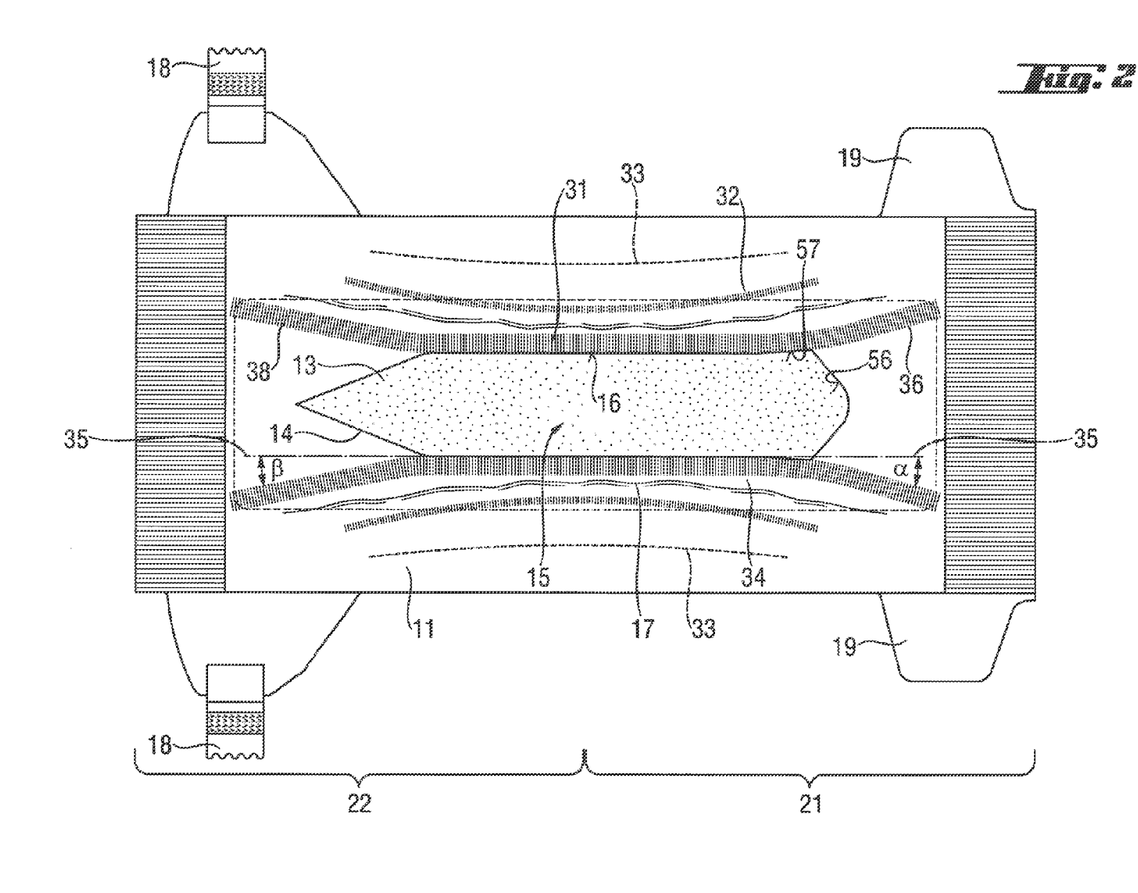
FIGS. 2 and 5 show each a plane view of the two preferred absorbent articles of FIGS. 1 and 4, respectively.
Figure 5:
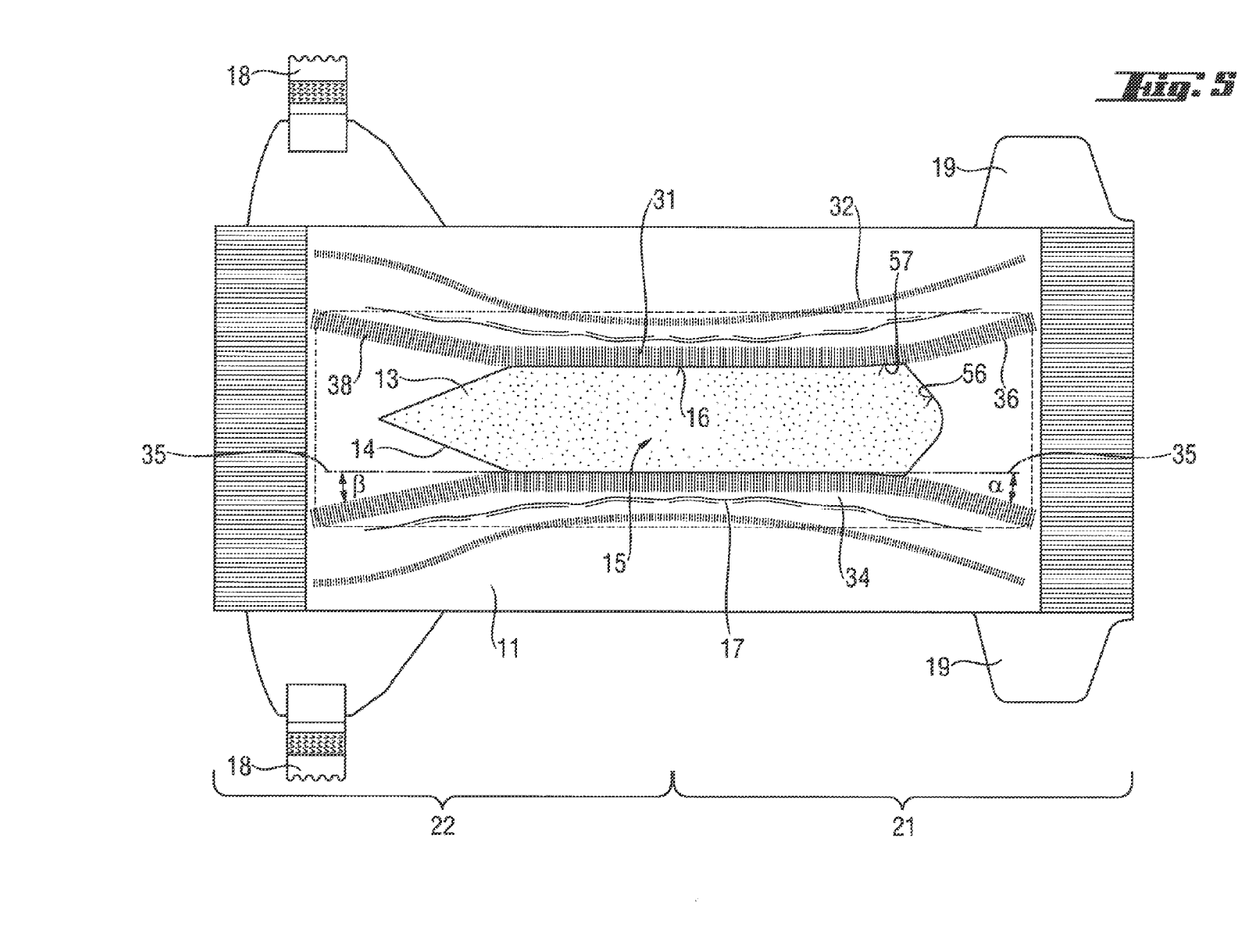

As shown in FIGS. 2 and 5, the primary elasticated areas (31) are preferably in the shape of an X, whereby each front end portion (36) of the elasticated area has an angle α with the longitudinal line (35) through that part of the elasticated area (31) (i.e. the centre region) that is (directly) adjacent a longitudinal side edge (16) of the opening (14), and parallel to the longitudinal axis of the topsheet (11). This angle α is preferably about 10° to 40°, or more preferably 20° to 30° in stretched state. Each back end portion (38) of the elasticated area (31) has an angle β with the longitudinal line (35) through that part of the elasticated area (31) that is (directly) adjacent a longitudinal side edge (16) of the opening (14). This angle β is also preferably about 10° to 40°, or more preferably 20° to 30° in stretched state.

The secondary elasticated areas (32) are curved, curving away from the opening (14), to provide a cross-machine direction (CD) elastical force on the opening (14) and the topsheet (11) as a whole, and ensuring a better anchoring of the topsheet (11) to the skin of the user, and a better alignment of the opening (14) with the anus (51) and genitals of the wearer (50) in use.

The topsheet (11) shown in FIGS. 1, 2, 4 and 5 is preferably made by making a longitudinal slit (58) with preferably no width dimension in the topsheet material (11) and cutting an additional front cut out section (55) out of the topsheet material (11), said section (55) extending from the front of this slit (58) towards the front of the diaper (10). This is further shown in FIGS. 3 and 6.

Preferably, the front cut out section (55) is 'diamond' shaped, although it is preferred that the 'diamond' shaped cut out section (55) has a front edge which is curved. The side edges extending directly from the slit (58) to the front edge of the diaper (10) and connecting the curved front edge with the slit (58) are preferably connected to one another with an angle γ (not shown), which is preferably between 40° and 140°, more preferably between 55° and 110°.

FIG. 3 also shows how the radius (R) of the curvature of a secondary elasticated area (32) is determined, by drawing a circle (curved line) through the end points of the secondary elasticated area (32) and through the closest point of the secondary elasticated area (32) (i.e. transversely closest to the primary elasticated area (31)), and determining the centre point of said circle and the length of the radius (R) of said circle, which is at least 0.3 times the length L of the absorbent article (10) (and typically of the topsheet) and at the most 3.2 times the length of the article (10).

Figure 7:
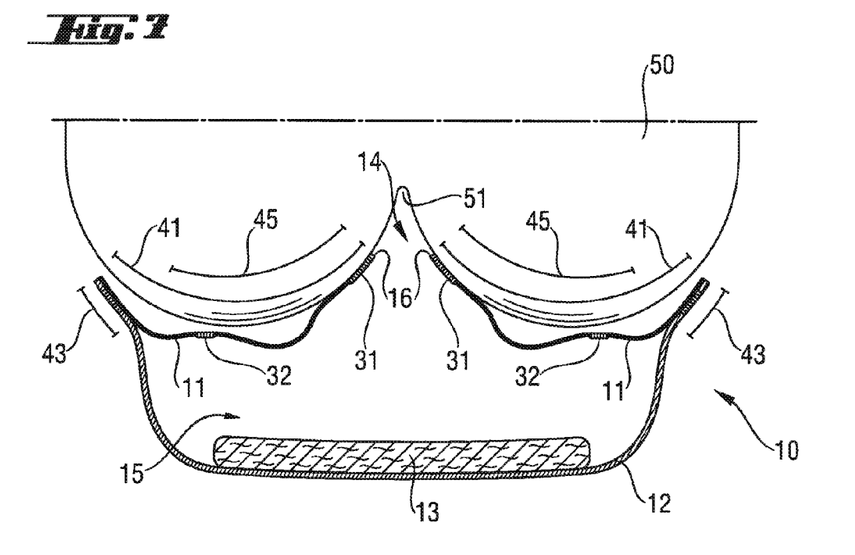
FIGS. 7 and 8 show each the preferred diaper of FIG. 1 in use, applied to a baby.
Figure 8:
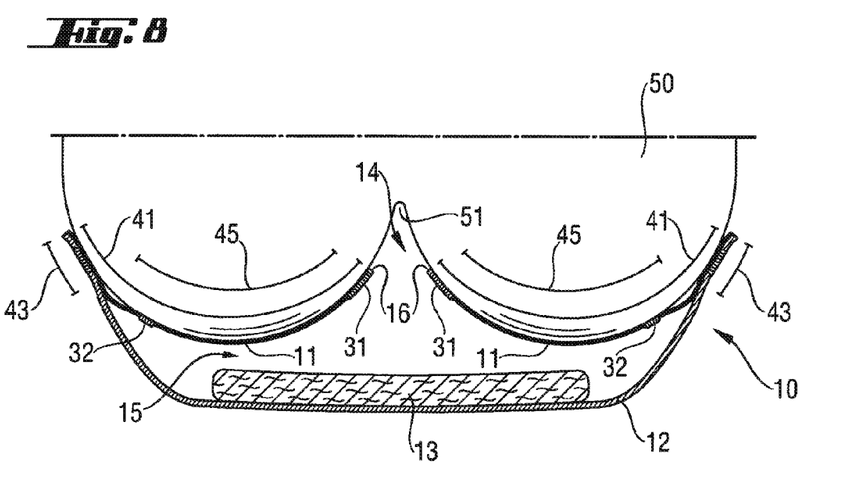

FIGS. 7 and 8 show a cross sectional view of the preferred diaper (10) of FIG. 1, applied to a baby, showing the baby's anus (51) and bottom (50), and showing how the elasticated areas (31, 32) are 'anchored', e.g. attached or in close contact with the skin of the baby in use. The presence of the secondary elasticated areas (32) further ensure that the opening (14) stays aligned with the anus (51) and that he topsheet (11) is pulled against the skin of the user, so the risk of feces leakage is further reduced.

Figure 9:
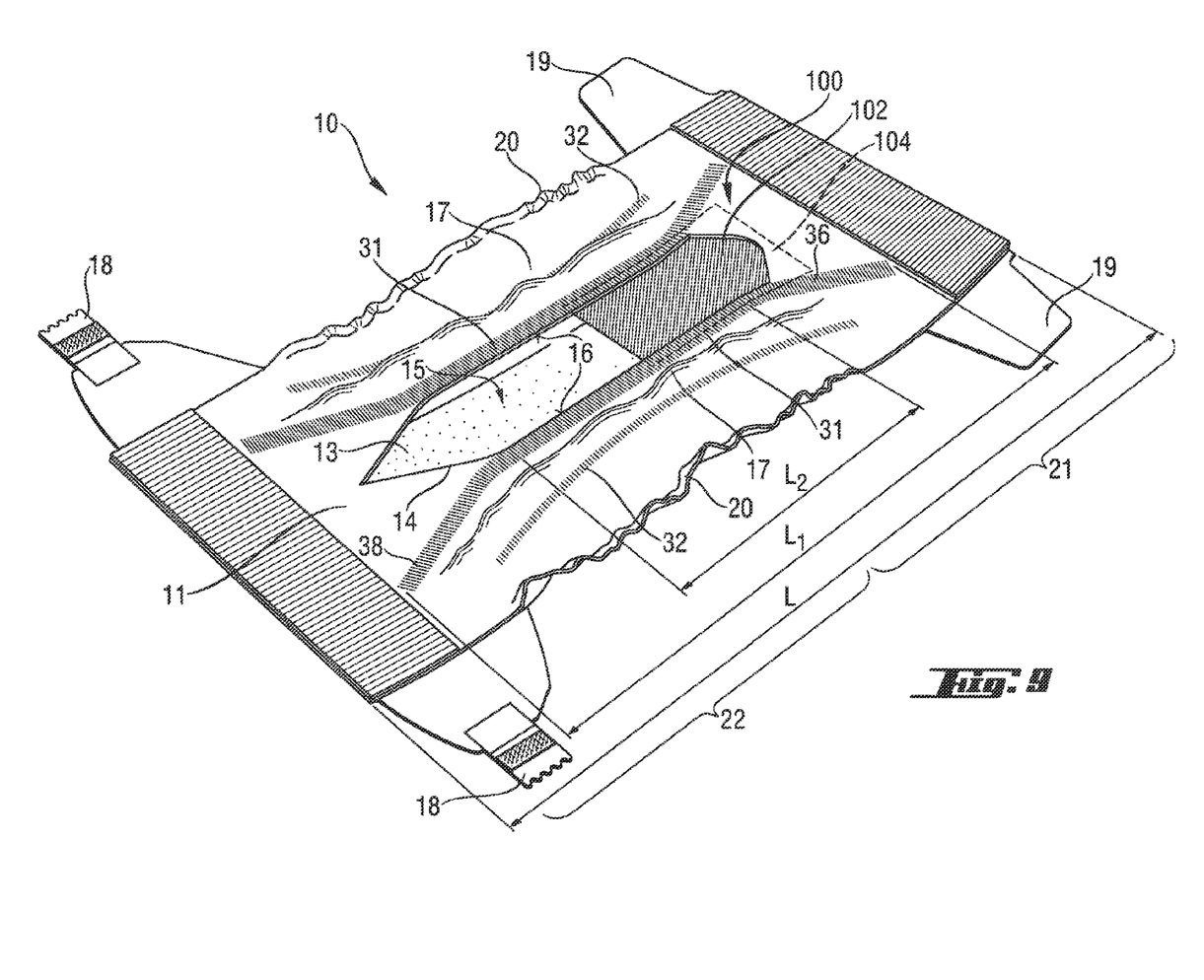
FIG. 9 shows an exemplary absorbent article having a genital coversheet.

FIG. 9 shows an exemplary absorbent article 10 having a genital coversheet 100. As shown in FIG. 9, the genital coversheet 100 is disposed under topsheet 11 and below the opening 14 in the topsheet 11. The coversheet 100 is partially attached to topsheet 11, forming attached areas 104 and at least one unattached area 102.

All documents cited are, in relevant part, incorporated herein by reference; the citation of any document is not be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications that are within the scope of this invention.

What is claimed is:

1. A disposable absorbent article comprising:
a backsheet;
a topsheet;
a core disposed between the topsheet and the backsheet; and
a genital coversheet;
the topsheet comprising:
an opening comprising first and second side edges, generally opposing each other, the opening providing a passageway to a void space for receiving bodily exudates therein, wherein the void space is positioned between the topsheet and the absorbent core, and first and second primary elasticated areas extending generally longitudinally adjacent to the first and the second side edges, wherein the topsheet comprises a secondary elasticated area;
wherein the genital coversheet is disposed under the topsheet and below the opening, such that the coversheet is partially attached to the topsheet in order to form attached areas and at least one non-attached area to cover and protect a user's genitals, further wherein, in stretched state, the primary elasticated areas comprise a front end portion, a back end portion and a center portion, wherein at least one of the back end portions and/or at least one of the front end portions are generally angled, such that a line along one of the back end portions and/or the front end portions intersects with a line parallel to a longitudinal axis of the topsheet and along at least one of the center portions of at least one of the primary elasticated areas, such that the acute angle of the intersection is from about 10° to about 40°.

2. A disposable absorbent article comprising:
a backsheet;
an absorbent core;
a topsheet, comprising:
a) a pair of generally longitudinal side edges;
b) a primary elasticated area comprising a first elastic portion and a second elastic portion, each of the first and second elastic portions comprising a front end portion and a center portion, wherein the front end portion of the first elastic portion bends away from the front end portion of the second elastic such that the distance between the front end portions of the first and second elastic portions is larger than the distance between center portions of first and second elastic portions; and
c) an opening that provides a passageway to a void space for receiving bodily exudates therein, said void space being positioned between the topsheet and the absorbent core; and
a genital coversheet disposed under the topsheet and below the opening such that the coversheet is partially attached to the topsheet in order to form attached areas and at least one non-attached area to cover and protect a user's genitals.

3. The absorbent article of claim 2, wherein the opening in a stretched state has an average width which is 10% to 25% of an average width of the absorbent article.

4. The absorbent article of claim 2, wherein the topsheet further comprises a secondary elasticated area comprising a first elastic portion and a second elastic portion, wherein a first elastic portion of the secondary elasticated area has a point which is transversely closest to a first elastic portion of the primary elasticated area on the same crotch side portion, wherein the transverse distance from the point is from 0.5 mm to 30 mm, and wherein the average transverse distance between the first portion of the secondary elasticated area and the first portion of the primary elasticated area is at least about 15 mm.

5. The absorbent article of claim 2, wherein in stretched state, each of the first and second elastic portions further comprise a back end portion, wherein each of the back end portions and the front end portions are angled from the longitudinal axis of the topsheet from about 10° to about 40°.

6. The absorbent article of claim 2, wherein each of the back end portions and the front end portions are angled from the longitudinal axis of the topsheet from about 17° to about 35°.

7. The absorbent article of claim 2, wherein a part of the genital coversheet below the opening has a maximum length of 10% to 50% of the maximum length of the opening.

8. The absorbent article of claim 2, wherein the genital coversheet is not attached to the absorbent core.

9. The absorbent article of claim 2, wherein the genital coversheet is extendable.

10. The absorbent article of claim 9, wherein the genital coversheet is non-elastically extendable.

* * * * *

UNITED STATES PATENT AND TRADEMARK OFFICE
CERTIFICATE OF CORRECTION

| | | |
|---|---|---|
| PATENT NO. | : 7,771,408 B2 | Page 1 of 1 |
| APPLICATION NO. | : 11/894087 | |
| DATED | : August 10, 2010 | |
| INVENTOR(S) | : Joerg Mueller et al. | |

It is certified that error appears in the above-identified patent and that said Letters Patent is hereby corrected as shown below:

<u>Column 13</u>

Line 9, delete "200" and insert --20°--.

Signed and Sealed this
Twenty-third Day of August, 2011

David J. Kappos
*Director of the United States Patent and Trademark Office*